United States Patent
Keller

(10) Patent No.: US 7,963,971 B2
(45) Date of Patent: Jun. 21, 2011

(54) INSTRUMENTATION FOR INSERTION OF AN INTER-VERTEBRAL PROSTHESIS

(75) Inventor: Arnold Keller, Kayhude (DE)

(73) Assignee: DePuy Spine, Inc., Raynham, MA (US)

(*) Notice: Subject to any disclaimer, the term of this patent is extended or adjusted under 35 U.S.C. 154(b) by 1667 days.

(21) Appl. No.: 10/493,888

(22) PCT Filed: Oct. 28, 2002

(86) PCT No.: PCT/EP02/12025
§ 371 (c)(1),
(2), (4) Date: Dec. 30, 2004

(87) PCT Pub. No.: WO03/037230
PCT Pub. Date: May 8, 2003

(65) Prior Publication Data
US 2005/0119665 A1 Jun. 2, 2005

(30) Foreign Application Priority Data

Oct. 29, 2001 (EP) .................................. 01125793
Jun. 10, 2002 (DE) .................................. 102 25 703

(51) Int. Cl.
*A61B 17/58* (2006.01)
*A61B 17/60* (2006.01)
*A61F 2/00* (2006.01)

(52) U.S. Cl. ........................................................ 606/99

(58) Field of Classification Search .................. 606/90, 606/99, 86 A, 105, 205–208, 914; 81/302, 81/312
See application file for complete search history.

(56) References Cited

U.S. PATENT DOCUMENTS

| 4,997,432 | A | * | 3/1991 | Keller ........................ 623/17.11 |
| 5,122,130 | A | * | 6/1992 | Keller ........................... 606/86 A |
| 6,478,800 | B1 | * | 11/2002 | Fraser et al. ..................... 606/99 |
| 6,551,316 | B1 | | 4/2003 | Rinner et al. |
| 6,716,218 | B2 | | 4/2004 | Holmes et al. |
| 7,118,580 | B1 | * | 10/2006 | Beyersdorff et al. ........... 606/99 |
| 2001/0031536 | A1 | * | 10/2001 | Shenoy ......................... 438/296 |
| 2002/0116009 | A1 | | 8/2002 | Fraser et al. |
| 2004/0002758 | A1 | | 1/2004 | Landry et al. |
| 2004/0093021 | A1 | | 5/2004 | Hanson |
| 2004/0106927 | A1 | | 6/2004 | Ruffner et al. |

FOREIGN PATENT DOCUMENTS

| DE | 198 36 498 | | * | 8/1998 |
| DE | 299 16 078 | U | | 11/1999 |
| DE | 198 36 498 | A1 | | 2/2000 |
| DE | 200 04 812 | U | | 9/2000 |
| DE | 20116410 | U1 | | 11/2001 |
| EP | 0269935 | A2 | | 6/1988 |
| EP | 0 333 990 | A1 | | 9/1989 |
| WO | WO 0119295 | A1 | * | 3/2001 |

* cited by examiner (Continued)

Primary Examiner — Eduardo C Robert
Assistant Examiner — Sameh Boles
(74) Attorney, Agent, or Firm — Nutter McClennen & Fish LLP

(57) ABSTRACT

An instrument for inserting an intervertebral prosthesis, comprising two prosthesis holders which are connected by a parellel guide and can be spread apart from one another and are intended to receive a pair of prosthesis plates. The first prosthesis holder is arranged fixedly on an elongate instrument body. The second prosthesis holder is held from the instrument body by means of a parallel guide. The parts connecting the second prosthesis holder to the instrument body or to the first prosthesis holder delimit on both sides a central through-opening which extends like a channel in the longitudinal direction of the instrument body and whose width corresponds at least to the transverse dimensions of a prosthesis core, to be inserted between the prosthesis plates, and of the prosthesis core holder provided for this.

18 Claims, 7 Drawing Sheets

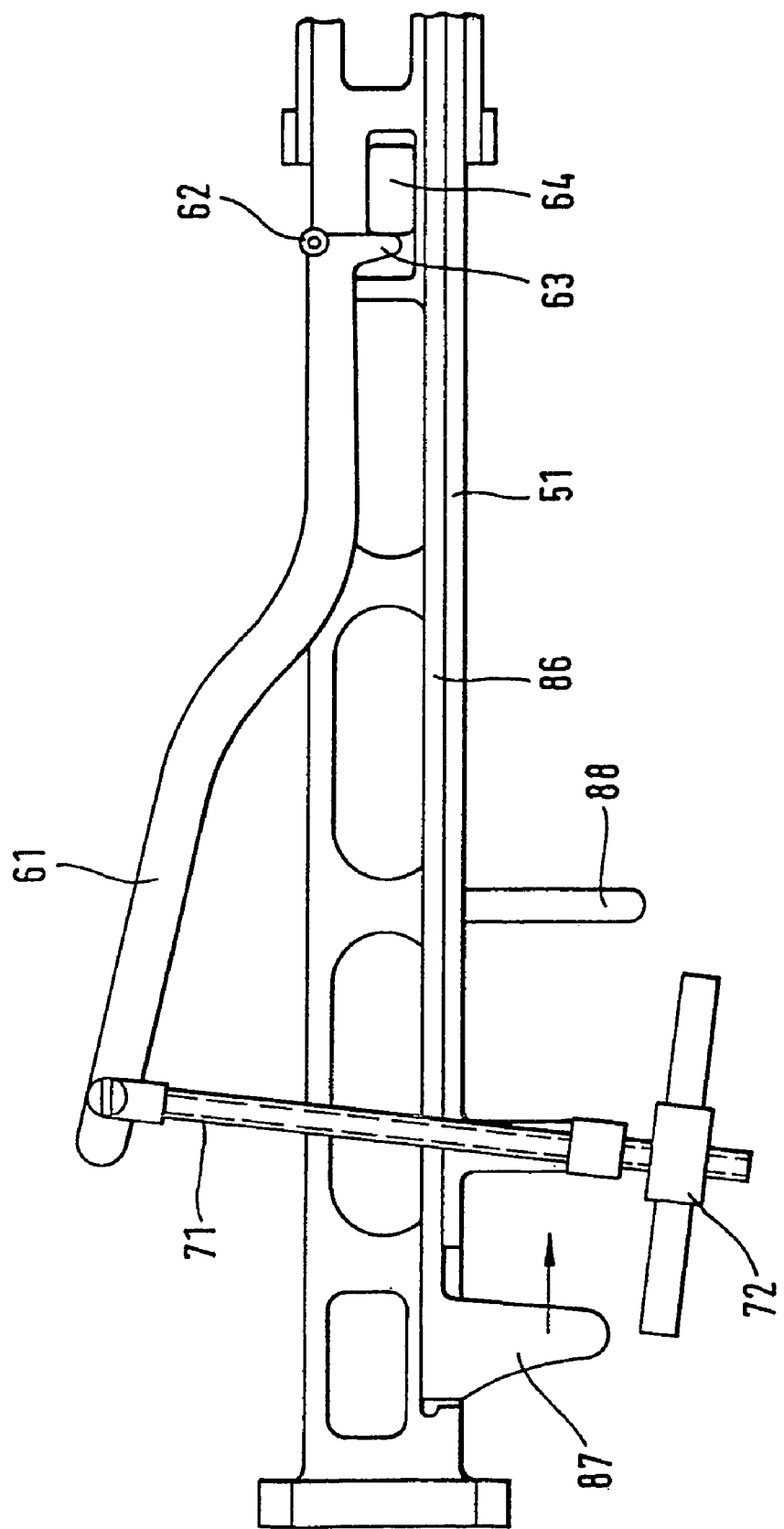

INSTRUMENTATION FOR INSERTION OF AN INTER-VERTEBRAL PROSTHESIS

BACKGROUND OF THE INVENTION

To insert intervertebral prostheses consisting of two prosthesis plates, each to be connected to a respective vertebral body, and of a prosthesis core arranged between these plates, insertion instruments are known (EP-A-333 990) which, at their front end, have two prosthesis holders which each receive a prosthesis plate. The prosthesis holders are connected to one another via a parallel guide which makes it possible initially to bring the prosthesis plates very close to one another, so as to be able more easily to introduce them into the narrow intervertebral space, and then to spread them apart (with the adjoining vertebrae) in order to be able to insert the prosthesis core between them. Thereafter, the prosthesis holders are moved back toward one another so that the prosthesis plates receive the prosthesis core in its operational position, and the instrument is removed. The known instrument is designed as a forceps which is angled in relation to the direction of the prosthesis holders, which direction is intended to coincide with the median direction of the body, so as not to impede the introduction of the prosthesis core. Nevertheless, the introduction of the prosthesis core is difficult.

An instrument for introducing a prosthesis of this kind is also known (DE-U-299 16 078) which is formed by a lower pair of guide rods and an upper guide rod, these rods being articulated on one another at the rear end and carrying prosthesis holders at their front ends. They form a guide track for a spreader element. When the latter is driven forward between them by means of a toothed rack, it spreads the rod ends apart and at the same time pushes the prosthesis core ahead of it until the latter has reached the desired end position. Thereafter, the spreader element is drawn back in order to bring the prosthesis plates toward the prosthesis core. In this case, the spreading movement is inextricably linked with the introduction of the prosthesis core, so that the spreading operation is not separate from the introduction of the prosthesis core and can be observed only with difficulty.

SUMMARY OF THE INVENTION

The object of the invention is to make available an instrument which permits spreading of the prosthesis plates independently of the introduction of the prosthesis core, but which still facilitates said introduction of the prosthesis core.

The solution according to the invention lies in the features of claim 1.

It relates to an instrument for inserting an intervertebral prosthesis, comprising two prosthesis holders which are connected by a parellel guide and can be spread apart from one another and are intended to receive a pair of prosthesis plates. The first of these prosthesis holders is arranged fixedly on an elongate instrument body so as to lie in the longitudinal direction of the latter. The second prosthesis holder is held on the instrument body by means of the parallel guide. All the parts connecting the instrument body and the second prosthesis holder are arranged outside a central through-opening which extends in the longitudinal direction of the instrument body and whose width corresponds at least to the transverse dimensions of the prosthesis core, to be inserted between the prosthesis plates, and of a prosthesis core holder provided for this. In this way, the prosthesis core can be easily introduced with the aid of a prosthesis core holder through the insertion instrument, whose elements on both sides form a guide for the prosthesis core or prosthesis core holder. To ensure that the operating surgeon, when introducing the prosthesis core, can easily detect the position of the prosthesis core holder at which the prosthesis core has reached the desired position between the prosthesis plates, the insertion instrument and the prosthesis core holder are expediently provided with interacting limit stops which determine this end position.

For actuation, an oblique link arm can be provided whose first end is mounted on the instrument body so as to be movable in the longitudinal direction thereof. Its second end is mounted on the second prosthesis holder with a fixed axis. Its first end is connected to an actuating device which is movable in the longitudinal direction of the instrument body. When the actuating device is moved in the direction in which the first end of the oblique link arm is moved in the direction toward the hinge point of its second end, the oblique link arm straightens and thus spreads the second prosthesis holder away from the instrument body and the first prosthesis holder, and vice versa.

The oblique link arm can be part of a scissor-type parallel guide. The oblique link arm is expediently provided in a pair symmetrically on both sides of the instrument body, in order to avoid a force transmission which is asymmetrical and tends to cause tilting.

The actuating device expediently comprises a handle and a transmission device. The transmission device can, for example, be formed by a threaded spindle. It has proven expedient to design the actuating device as a grip lever which is connected to a shorter working lever forming the transmission device. It is expediently arranged in such a way that it at the same time converts the lateral movement of the grip lever into the actuating direction extending in the longitudinal direction of the instrument body.

The oblique link arm can be mounted with its first end on a slide which is guided on the instrument body in the longitudinal direction thereof. Instead of this, it is also possible for the oblique link arm to be a member of a toggle lever pairing, in which case the actuating device acts directly or indirectly on the toggle point of the lever pairing.

In another embodiment of the invention, an actuating device is provided which comprises an actuating lever which is mounted at its front end on the instrument body or the first prosthesis holder so as to pivot. The pivot axis extends transversely with respect to the longitudinal direction of the instrument body and to the direction of spreading. Behind this axis, the lever has a limit stop which acts directly or indirectly on the second prosthesis holder. At the rear end, the lever is designed such that it can be operated by hand. In the unspread state of the instrument, the lever is at a certain angular distance from the instrument body. If it is pulled by hand, or by suitable aids such as a threaded spindle, toward the instrument body, the limit stop moves the second prosthesis holder away from the first prosthesis holder and in this way spreads them apart. By virtue of the lever action, great spreading forces can be transmitted. In a preferred embodiment of the invention, the limit stop acts on an oblique link arm connected to the second prosthesis holder, which oblique link arm can also be part of the parallel guide. The lever is expediently not an integral part of the instrument body, and instead it is designed in such a way that it can be easily attached to the instrument body and released again from the latter during the operation. This has the advantage that the instrument body is not weighed down by the spreader mechanism, formed by the lever, in those stages of the operation when spreading does not take place or does not have to be maintained. This actuating device may merit protection independently of the features of the claims.

BRIEF DESCRIPTION OF THE DRAWINGS

The invention is explained in greater detail below with reference to the drawing which depicts an advantageous illustrative embodiment. In said drawing:

FIG. 5 shows a bottom view of the rear part of the instrument.

DESCRIPTION OF THE PREFERRED EMBODIMENTS

At the front end of the instrument body 51 there are two holders 52 for prosthesis plates 53. The prosthesis holders 52 are fork-shaped and open at the end. Their side branches form guides for the edge of the prosthesis plates 53. Their direction coincides with the longitudinal direction of the instrument body. They allow the prosthesis plates to overcome a frictional force and be inserted easily into the prosthesis holders 52, and removed therefrom, in the longitudinal direction of the instrument. At the rear end, the prosthesis body 51 has a strike plate 54. By striking this plate, the prosthesis plates 53 held by the prosthesis holders 52 can be driven in between two vertebral bodies.

Figure 1:
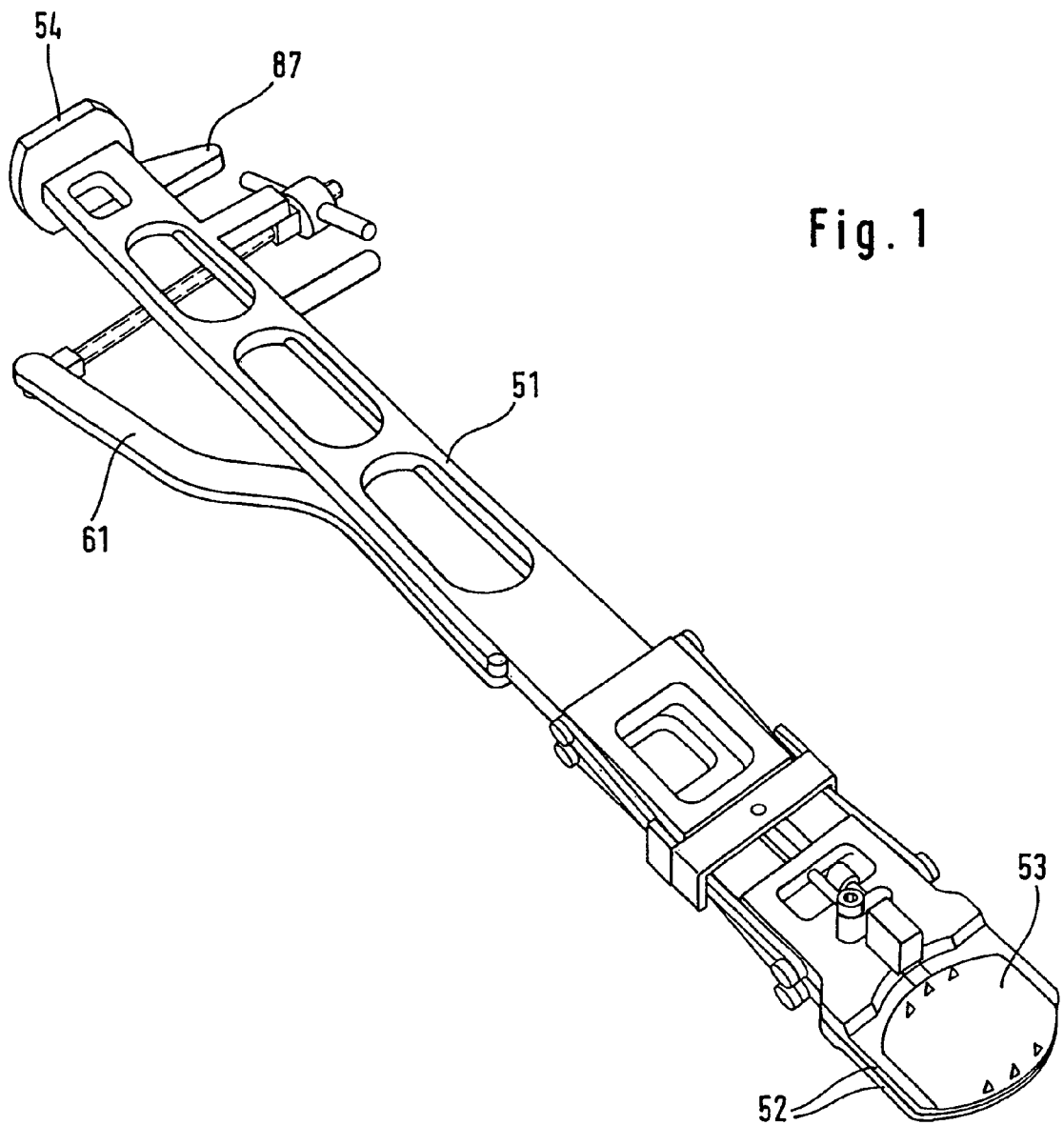
FIG. 1 shows an overview of the instrument.
Figure 2:
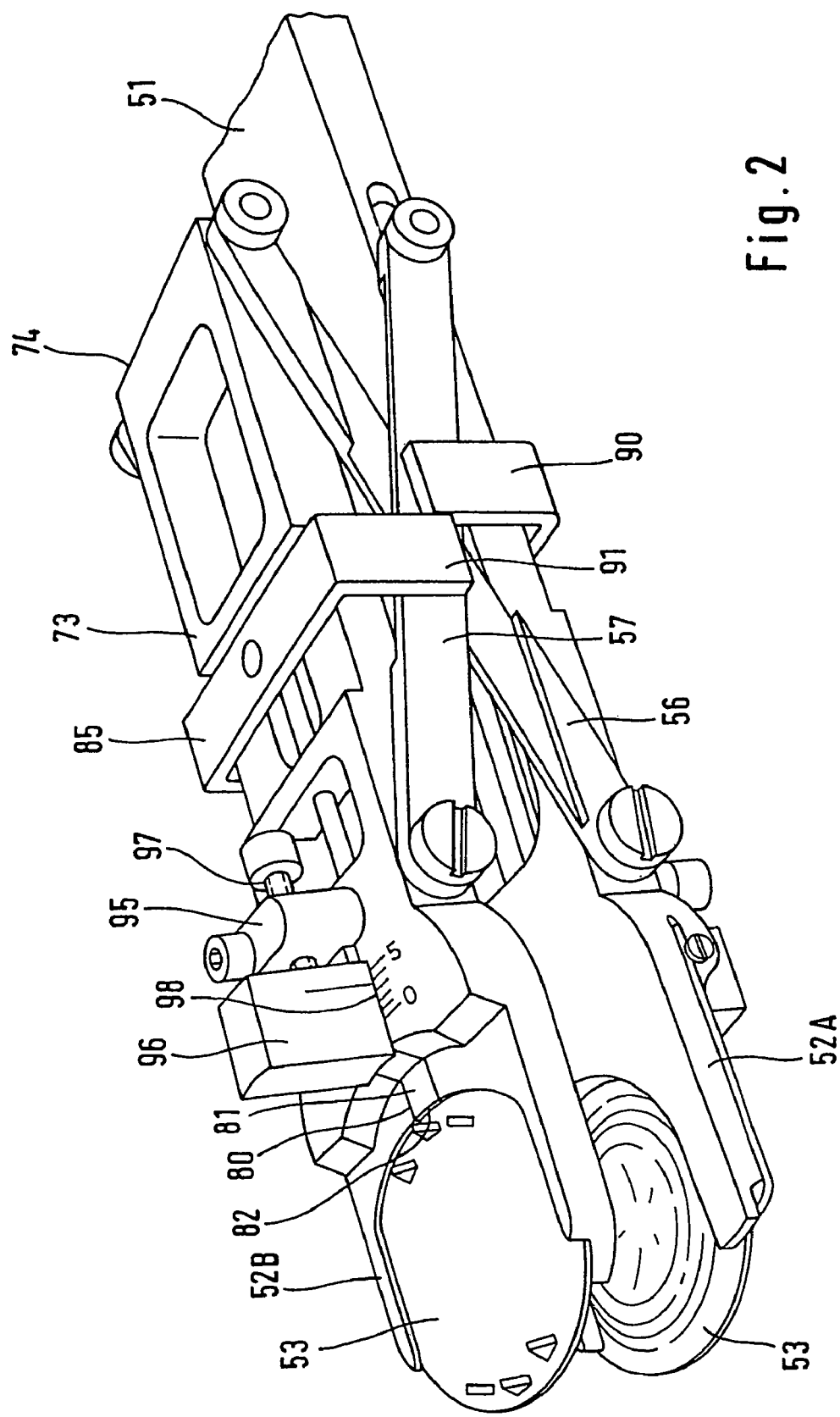
FIG. 2 shows a perspective view of the front portion of the instrument, obliquely from above.

The lower prosthesis holder 52A (FIGS. 9 and 10) is fixedly connected to the instrument body 51, and in the example illustrated is even made integral therewith. The upper prosthesis holder 52B is connected to the instrument body 51 via a scissor arrangement consisting of scissor members 56, 57. The scissor arrangement 56, 57 is provided as a pair on both sides of the instrument body and is designed in such a way that the upper prosthesis holder 52B can move exclusively perpendicular to the lower prosthesis holder 52A and parallel to it. The prosthesis holders can be brought very close to one another (FIG. 1) so that it is easier to drive them into the intervertebral space. They can be spread apart (FIGS. 2 and 3) together with the adjoining vertebral bodies in order to create space for introducing the prosthesis core 77 between the prosthesis plates 53. They are then brought back toward each other in order to secure the prosthesis core in the desired position. The instrument can then be removed.

Figure 6:
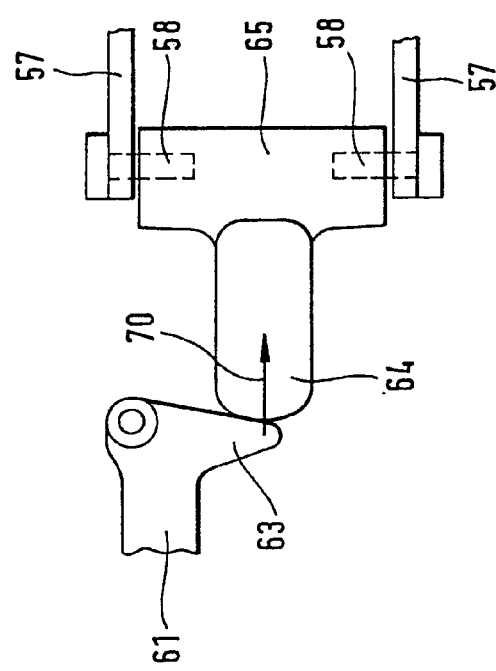
FIG. 6 shows a detail of the actuating device.

The rear pins 58, 59 of the scissor members 56, 57 slide in oblong holes of the instrument body 51 or of the plate 73 which continues the upper prosthesis holder 52B to the rear. The direction of the oblong holes coincides with the longitudinal direction of the instrument. The front pins 60 of the scissor members 56, 57 are rigidly connected to the prosthesis holders 52. In order to spread the prosthesis holders, a device is provided which moves the rear pin 58 of the scissor member 57 in the longitudinal direction of the instrument. For this purpose, the grip lever 61 is provided which is pivotable on the instrument body about an axis 62 and has a working lever 63 acting on the rear end of a slide block 64, which is part of a T-shaped slide 65 (FIGS. 4 and 6) on whose crosshead the rear pins 58 of the scissor members 57 arranged on both sides are articulated. The slide 65 is guided in the longitudinal direction of the instrument body. It will be seen in FIG. 4 that the parallel edges of the slide block 64 are guided between correspondingly parallel edges 66 of a cutout in the instrument body. It will be seen in FIG. 3 that the ends 67 of the crosshead are guided in oblong holes 68. When the grip lever 61 is pulled toward the instrument body, as when pressing together the levers of a forceps, its working lever 63 pushes the slide 64 in the arrow direction 70 (FIG. 6). In this way, the rear end of the scissor member 57 is driven forward, as a result of which the prosthesis holders 52 are spread apart from one another. The working lever 63, the slide 65 and the oblique link arms 57 thus form an arrangement for adjusting the distance between the prosthesis holders 52. It will be appreciated that this arrangement can also be replaced by other designs. It will also be noted that the spreading force does not necessarily have to be exerted via parts of the scissor arrangement.

Figure 7:
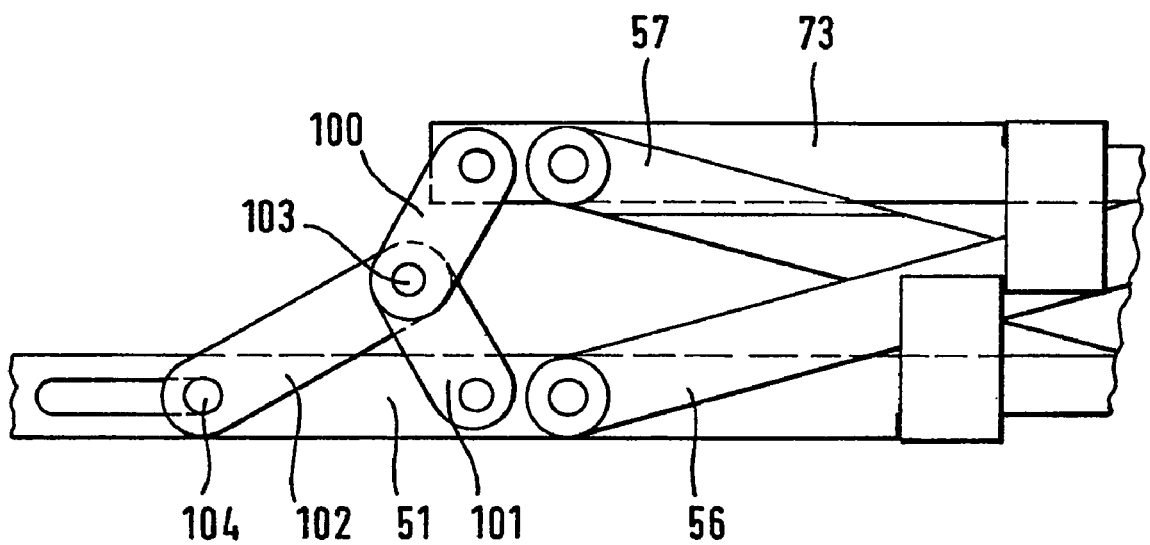
FIG. 7 shows a second design of the spreader device.

If the angle between the oblique link arm 57 and the longitudinal direction of the instrument is too small for exerting a substantial spreading force, a separate member can be provided for the spreading. This alternative is illustrated in FIG. 7. The plate 73, which at its front end supports the upper prosthesis holder 52, is supported, as in the above-described illustrative embodiment, by means of a scissor arrangement 56, 57 on the instrument body 51. In a departure from this design, the spreading device is made independent of the scissor arrangement. The link arms 100, 101 form a toggle lever arrangement. One end of these link arms is connected to the instrument body 51 or the plate 73. Their other end forms the toggle 103, on which the end of a link arm 102 engages whose other end 104 is connected to the actuating device. The connection can be configured as shown in FIG. 6. The spreading arrangement independent of the scissor arrangement 56, 57 has the advantage that the angles at which the link arms 100, 101 and 102 are stressed can be dimensioned solely for favorable force transmission and without taking into account a parallel guide function.

Considerable forces arise when the prosthesis holders are spread apart. For this reason, the grip lever 61 is supplemented by a threaded spindle 71 with butterfly nut 72, which makes the procedure easier and allows the instrument to be fixed temporarily in the spread position.

Figure 3:
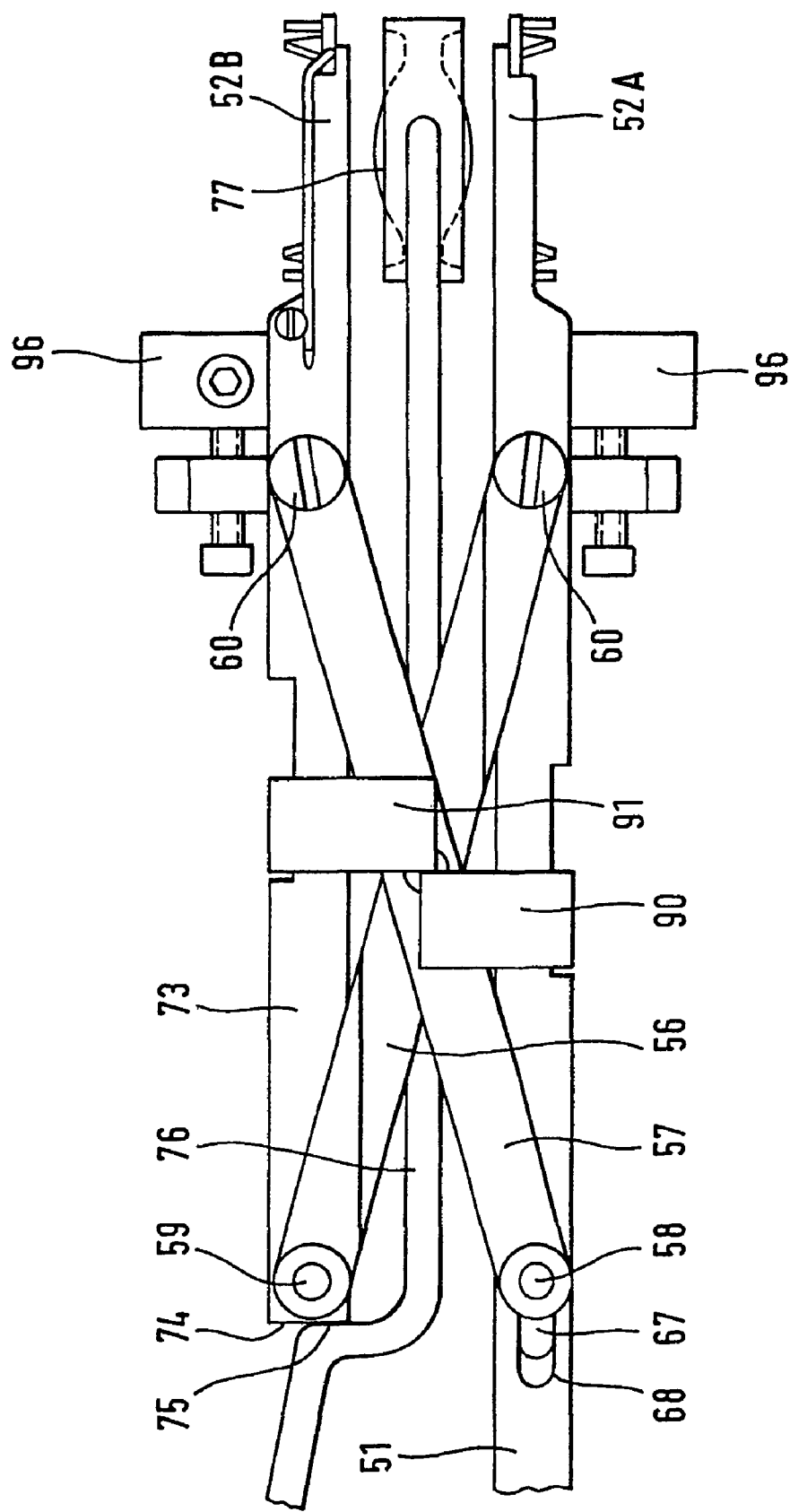
FIG. 3 shows a side view of the front portion.

In this position, a channel-like free space is formed between the instrument body 51 and the plate 53 continuing the upper prosthesis holder 52 rearward, on the one hand, and between the lateral scissor arrangements 56, 57 on the other hand. Using an instrument 76 guided between the link arms 56, 57, the prosthesis core 77 can be guided through this free space between the prosthesis plates 52 (FIG. 3). The instrument 76 has a limit stop 75 which bears on the rear edge 74 of the plate 73 when the prosthesis core 77 has exactly reached the intended position between the prosthesis plates 52.

Figure 4:
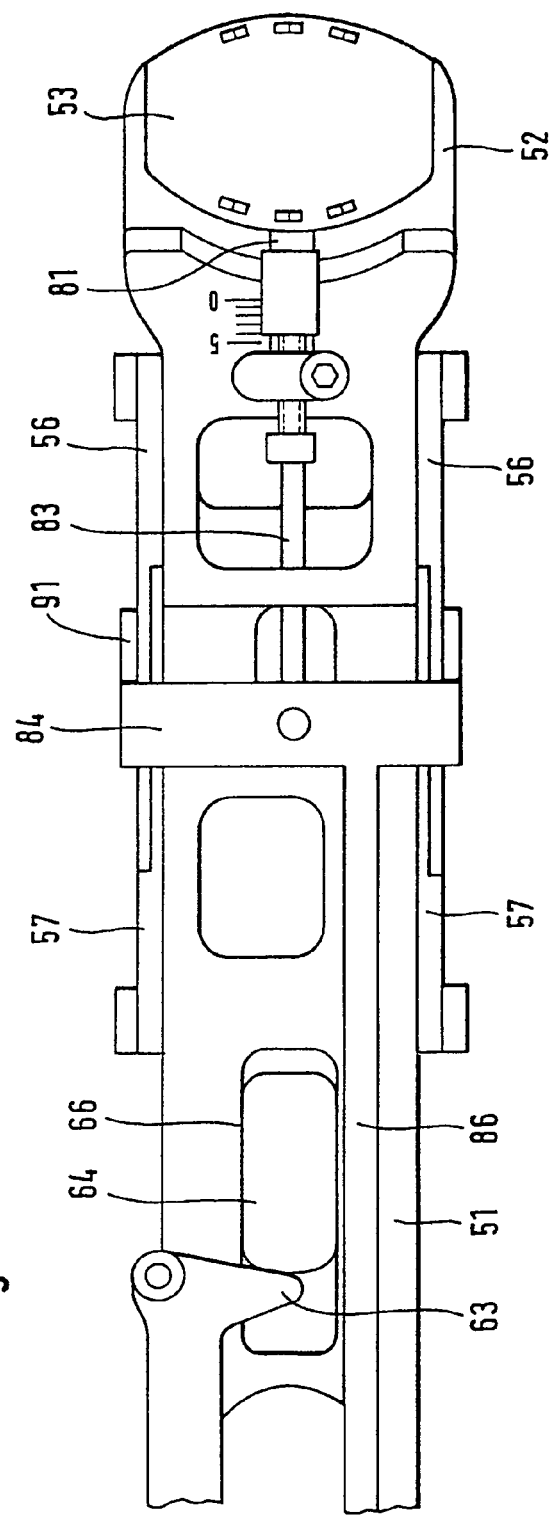
FIG. 4 shows a bottom view of the front portion.

A device is now described which is used to eject the prosthesis plates 53 from the prosthesis holders 52 and to force the instrument away from the prosthesis holders and the adjoining vertebrae. Behind the receiving area for the prosthesis plates 53, the prosthesis guides 52 contain a guide groove 80 which extends in the longitudinal direction of the instrument and thus in the direction of sliding of the prosthesis holders 52. It includes a slide 81 whose front end 82 strikes against the edge of the prosthesis plate located in the prosthesis holder and is therefore referred to as a prosthesis limit stop. The rear end (not visible in FIGS. 2 and 3) of the slide 81 is rigidly connected to rods 83 likewise guided in the longitudinal direction of the instrument. The rear end of the rod 83 mounted in the instrument body 51 is, as shown in FIG. 4, secured on a limit stop element 84 whose nature will be explained later. It is also displaceable in the longitudinal direction of the instrument. The limit stop element 84 is in turn rigidly connected to a push rod 86 which is mounted so as to be longitudinally displaceable in the instrument body 51 and leads to a handle 87. When the operating surgeon pushes the handle 87 forward in the direction of the arrow, the push rod 86, the limit stop element 84, the rod 83 and the slide 81 are moved forward in order to push the prosthesis plate 53 out of the prosthesis holder 52. In doing so, the operating surgeon's hand can be supported on a projection 88 which is fixedly connected to the instrument body 51.

The movement of the handle 87 acts directly only on the slide 81 which is arranged in the lower part of the instrument, namely in the instrument body. To ensure that the slides 81 of both prosthesis holders move in synchrony, a movement-transmitting device is provided. The rod 83 controlling the slide 81 of the upper prosthesis holder is fixedly connected at its rear end to a limit stop element 85 which, like the limit stop element 84 of the lower prosthesis holder, is guided movably in the longitudinal direction of the instrument. The lower limit stop element 84 has, on both sides, upwardly extending limit stop branches 90 which lie behind and adjacent to the branches 91 which extend downward on both sides from the upper limit stop element 85. When the prosthesis plates 53 are located in their rearmost position in the prosthesis holders 52, and the prosthesis limit stops 82 touch them, the mutually adjacent end faces of the limit stop branches 90, 91 also bear on one another. If, by means of actuation of the handle 87, the lower limit stop element 84 is now pushed forward with the limit stop branches 90, the cooperation of these with the limit stop branches 91 of the upper limit stop element means that the slide 81 of the upper prosthesis holder is also pushed forward. The two slides 81 thus move in synchrony. Since the interacting limit stop surfaces 90, 91 are perpendicular to the longitudinal direction of the instrument, the synchronous movement of the slides 81 is ensured independently of the respective distance of the prosthesis holders from one another.

Each slide 81 carries a shoulder 95, rigidly connected to it, and also a small block 96 which is guided on the slide, in the longitudinal direction thereof, and whose front face forms the vertebral limit stop. When the prosthesis holders, with the prosthesis plates 53 contained in them, are driven into the intervertebral space between two vertebrae, the front faces of the vertebral limit stops 96 finally bear on the ventral margins of the vertebral bodies. The distance of the front faces of the vertebral limit stops 96 from the prosthesis plates thus determines the depth to which the prosthesis plates reach into the intervertebral space. This depth can be changed by adjusting the vertebral limit stops 96 on the slides 81. This is done by means of a threaded spindle 97 which is guided in a threaded bore of the shoulder 95 and whose end is rotatable, but connected fixedly to the vertebral limit stop 96 in the longitudinal direction. By turning the threaded spindle 97, the operating surgeon can thus predetermine the depth of insertion of the prosthesis plates 53 in relation to the ventral margin of the associated vertebral bodies. Scale markings 98 help him to do this.

Figure 8:
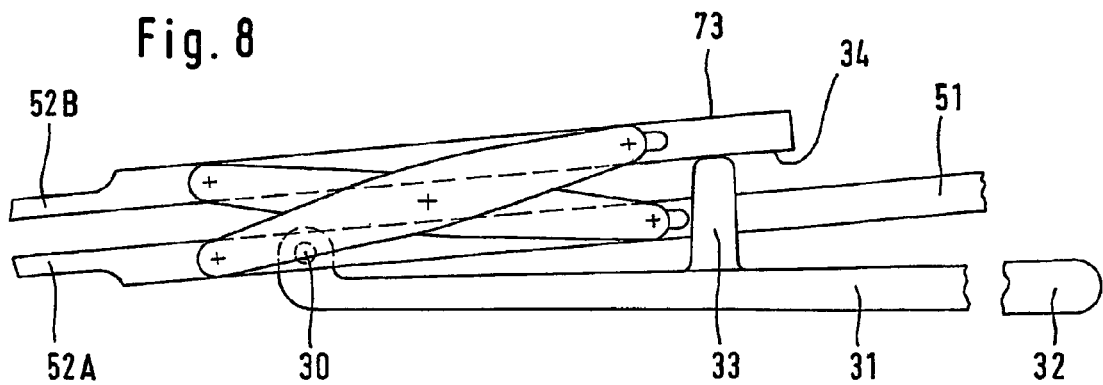
FIG. 8 shows a third design of the spreader device.

In the alternative design according to FIG. 8, the instrument body 51, near its front end, is connected via a pivot axis 30 to the front end of an actuating lever 31 which extends approximately parallel to the instrument body 51 and can be gripped at its rear end 32 in the manner of a forceps lever so as to be pressed toward the instrument body 51. It has a limit stop projection 33, or a pair of limit stop projections 33, located on both sides of the instrument body and extending toward an opposite limit stop surface 34 on the second prosthesis holder or on a plate 73 connected to the latter. When the prosthesis holders 52A, 52B are not spread apart, the actuating lever 31 runs at an acute angle away from the instrument body 51. When it is pressed toward the instrument body 51, the limit stop projection 33 lifts the prosthesis holder 52B in order to spread it apart from the prosthesis holder 52A.

Figure 9:
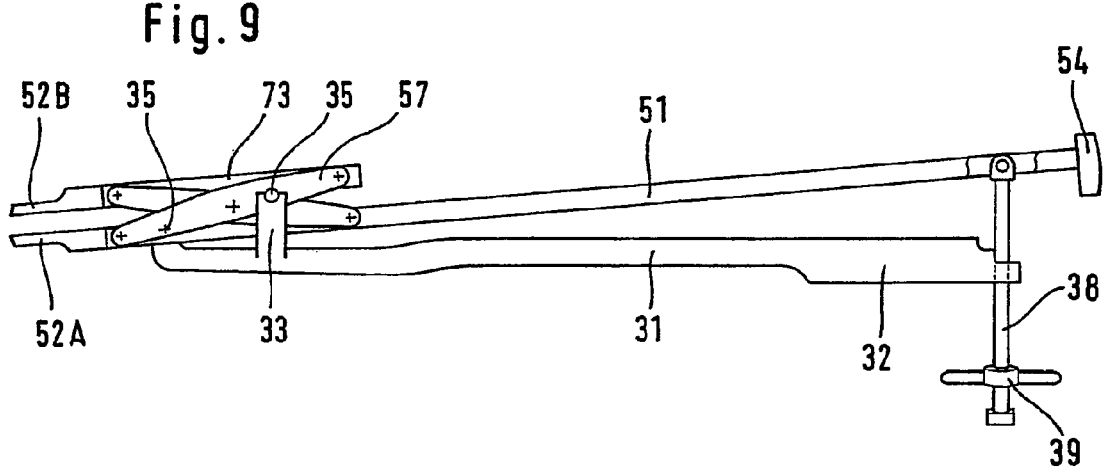
FIG. 9 shows a variant of the third design of the spreader device.
Figure 10:
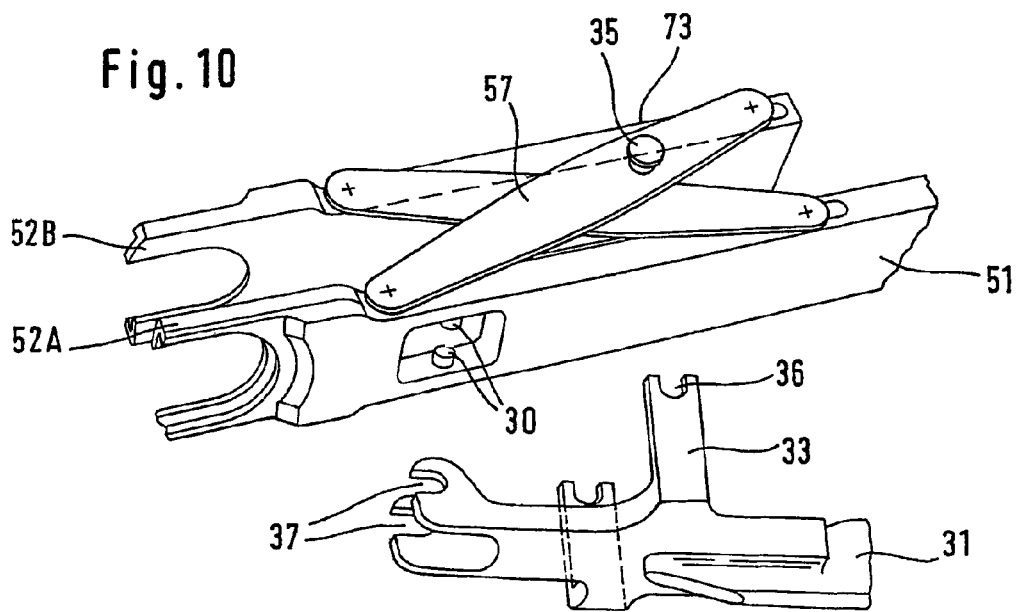
FIG. 10 shows a detail of the actuating lever used for this.

A similar design is shown in FIGS. 9 and 10. The same reference numbers designate identical parts. For their description, reference can be made to the above example.

The limit stop projection 33 does not engage directly on the plate 73, but instead on the link arm 52 which carries a limit stop pin 35 cooperating with a groove 36 at the end of the limit stop projection 33. For cooperation with the axis 30, an open receiving bore 37 is provided at the end of the actuating lever 31. The function is the same as that of the illustrative embodiment of FIG. 8. The difference lies in the fact that the engagement of the limit stop projection 33 on the oblique link arm 57 provides for a transmission, the order of which can be freely determined by the selection of the point of engagement. The design according to FIG. 9 also differs from that of FIG. 8 in that the actuating lever 31, by virtue of the open groove 36 and the open receiving bore 37, can be easily removed from the instrument body and can be easily coupled to it. As will be seen in FIG. 10, the limit stop projection 33, the limit stop pin 35, the axis 30 and the open receiving bore 27 are provided in pairs, in order to permit a secure connection to the instrument body and to ensure that the space between the parallel guides 56, 57 which serves for insertion of the prosthesis core is kept free from construction parts.

At the rear end 32, the actuating lever 31 can of course be operated by hand. In addition, however, a threaded spindle 38 is provided on which the actuating lever 31 can be brought close to the instrument body 51 with considerable force by means of a nut 39 and with the aid of which the spread position of the instrument can be secured. The actuating lever 31 can also be released from the instrument body in the area of the spindle 38.

What is clamed is:

1. An instrument set for inserting an intervertebral prosthesis, comprising:
    an instrument having:
        a first prosthesis holder and a second prosthesis holder, each holder being configured to receive a prosthesis plate;
        a parallel guide connected to the prosthesis holders and configured to spread the prosthesis holders apart from one another; and
        a prosthesis core holder configured for inserting a prosthesis core between the prosthesis plates;
    wherein, the first prosthesis holder is arranged fixedly on an elongate instrument body, and parts connecting the second prosthesis holder to at least one of the instrument body and the first prosthesis holder are configured to delimit on both sides a central through-opening that extends to form a channel in a longitudinal direction of the instrument body, wherein a width of the channel corresponds at least to the transverse dimensions of the prosthesis core holder and a prosthesis core for insertion between the prosthesis plates; and wherein the parts connecting the second prosthesis holder to at least one of the instrument body and the first prosthesis holder comprise oblique link arms that are configured to form at least a portion of the parallel guide.

2. The instrument set of claim 1, wherein the parts connecting the second prosthesis holder to at least one of the instrument body and the first prosthesis holder form a lateral guide for the prosthesis core holder.

3. The instrument set of claim 1, further comprising at least one interacting limit stop coupled to each of the instrument and the prosthesis core holder, the interacting limit stops being configured to define an end position of the prosthesis core holder.

4. The instrument set of claim 1, wherein the oblique link arms are provided in pairs and the pairs are symmetrically disposed on opposing sides of the instrument body.

5. The instrument set of claim 1, wherein the parallel guide is configured to be of a scissor-type.

6. The instrument set of claim 1, further comprising an actuating device, the actuating device further comprising:
   an actuating lever having a front end, wherein the front end is mounted on one of the instrument body and the first prosthesis holder so as to pivot about an axis extending transversely with respect to the longitudinal direction of the instrument body and to the direction of spreading; and
   a limit stop provided behind the axis and configured to act directly or indirectly on the second prosthesis holder.

7. The instrument set of claim 6, wherein the limit stop is configured to act on an oblique link arm connected to the second prosthesis holder.

8. The instrument set of claim 6, wherein the actuating lever is configured to be attached or released during operation of the instrument set.

9. The instrument set of claim 1, wherein a proximal end of the parallel guide is movably coupled to the instrument body and fixedly coupled to the second prosthesis holder.

10. An instrument set for inserting an intervertebral prosthesis, comprising:
    an instrument body;
    a first prosthesis holder fixedly connected to the elongate instrument body and configured to receive a prosthesis plate;
    a second prosthesis holder connected to the elongate instrument body and configured to receive a prosthesis plate;
    a parallel guide connected to the prosthesis holders such that the second prosthesis holder is connected to the elongate instrument body by the parallel guide, the parallel guide being configured to spread the prosthesis holders apart from one another and form a channel in a longitudinal direction of the instrument body; and a prosthesis core holder configured for inserting a prosthesis core between prosthesis plates received by the first and second prosthesis holders; and
    an oblique link arm having a first end and a second end;
    wherein the first end of the oblique link arm is mounted on the instrument body such that it is movable in a longitudinal direction thereof and the second end of the oblique link arm is mounted on the second prosthesis holder with a fixed axis, the first end of the oblique link arm being configured to be connected to an actuating device that is movable in a longitudinal direction of the instrument body; and
    wherein a width of the channel corresponds at least to the transverse dimensions of the prosthesis core holder and a prosthesis core for insertion between prosthesis plates received by the first and second prosthesis holders.

11. The instrument set of claim 10, wherein the actuating device comprises a handle and a transmission device.

12. The instrument set of claim 11, wherein the handle is formed by a grip lever and the transmission device is formed by a shorter working lever connected to the grip lever.

13. The instrument set of claim 10, wherein the first end is mounted on a slide guided on the instrument body in the longitudinal direction thereof.

14. The instrument set of claim 10, wherein the oblique link arm is a member of a toggle lever pairing.

15. The instrument set of claim 10, wherein the parallel guide comprises the oblique link arm and a second oblique link arm, the second oblique link arm being mounted on the first prosthesis holder with a fixed axis and the second prosthesis holder with a fixed axis.

16. An instrument for inserting an intervertebral prosthesis, comprising:
    an instrument body;
    a first prosthesis holder fixedly connected to the instrument body and configured to receive a prosthesis plate;
    a second prosthesis holder configured to receive a prosthesis plate;
    a parallel guide coupled to each of the instrument body, the first prosthesis holder, and the second prosthesis holder, the parallel guide including a first pair of oblique link arms and a second pair of oblique link arms, the first and second pairs of oblique link arms being symmetrically disposed on opposing sides of the instrument body, and the parallel guide being configured to slide longitudinally along the instrument body to spread the first and second prosthesis holders apart from one another and form a channel in a longitudinal direction of the instrument body; and
    a prosthesis core holder configured for inserting a prosthesis core between prosthesis plates received by the first and second prosthesis holders;
    wherein a width of the channel corresponds at least to the transverse dimensions of the prosthesis core holder and a prosthesis core for insertion between prosthesis plates received by the first and second prosthesis holders.

17. The instrument of claim 16, wherein the parallel guide is configured to be of a scissors-type.

18. The instrument of claim 16, further comprising:
    a first limit stop coupled to at least either the instrument body and the first prosthesis holder and having an end face; and
    a second limit stop coupled to the second prosthesis holder and having an end face, the end face of the second limit stop bearing against the end face of the first limit stop;
    wherein movement of the first and second limit stops toward distal ends of the first and second prosthesis holders results in prosthesis plates received by the first and second prosthesis holders being moved in a distal direction and movement of the first and second limit stops toward proximal ends of the first and second prosthesis holders indicates that at least one prosthesis plate is being moved in a proximal direction into at least one of the first and second prosthesis holders.

* * * * *